United States Patent
Lure et al.

(10) Patent No.: US 6,873,717 B2
(45) Date of Patent: Mar. 29, 2005

(54) INPUT/OUTPUT INTERFACE FOR COMPUTER AIDED DIAGNOSIS (CAD) SYSTEM

(75) Inventors: Fleming Y. Lure, Potomac, MD (US); Rongfeng Zhang, Gaithersburg, MD (US); Jyh-Shyan Lin, North Potomac, MD (US); Xin-wei Xu, Gaithersburg, MD (US); H. Michael Yeh, Potomac, MD (US)

(73) Assignee: Riverain Medical Group, LLC, Miamisburg, OH (US)

( * ) Notice: Subject to any disclaimer, the term of this patent is extended or adjusted under 35 U.S.C. 154(b) by 0 days.

(21) Appl. No.: 10/414,292

(22) Filed: Apr. 16, 2003

(65) Prior Publication Data

US 2004/0008876 A1 Jan. 15, 2004

Related U.S. Application Data

(60) Provisional application No. 60/394,239, filed on Jul. 9, 2002.

(51) Int. Cl.[7] .................................................. G06K 9/00
(52) U.S. Cl. .................................................... 382/128
(58) Field of Search ............................... 382/128–133; 128/921–923

(56) References Cited

U.S. PATENT DOCUMENTS

| | | | |
|---|---|---|---|
| 5,235,510 A | | 8/1993 | Yamada et al. |
| 5,799,101 A | * | 8/1998 | Lee et al. ................ 382/133 |
| 5,878,746 A | * | 3/1999 | Lemelson et al. .......... 128/922 |
| 5,917,929 A | | 6/1999 | Marshall et al. |
| 5,987,345 A | * | 11/1999 | Engelmann et al. ........ 382/130 |
| 6,246,745 B1 | * | 6/2001 | Bi et al. ..................... 382/132 |
| 6,283,761 B1 | * | 9/2001 | Joao .......................... 128/923 |
| 6,434,262 B2 | * | 8/2002 | Wang ........................ 382/132 |
| 6,606,400 B1 | * | 8/2003 | Takeo ........................ 382/128 |
| 6,630,937 B2 | * | 10/2003 | Kallergi et al. ............. 382/128 |

* cited by examiner

Primary Examiner—Jingge Wu
(74) Attorney, Agent, or Firm—Venable LLP; Robert Kinberg; Jeffrey W. Gluck (57) ABSTRACT

A user interface for facilitating a computer-aided diagnosis (CAD) includes an image input device that receives and scans the multiple images, and a film feeder that transports films from a film developer to the scanner. A multi-image identification input device uses bar code reading, numeric keypad, keyboard, network, and/or mouse to enter multiple image identification prior to image scanning. A display includes an image identification area, case processing status area, and a CAD detection and user modification area. The user can edit CAD results—accept, remove—and can add new diagnosis results to create a new composite diagnosis result.

21 Claims, 8 Drawing Sheets

INPUT/OUTPUT INTERFACE FOR COMPUTER AIDED DIAGNOSIS (CAD) SYSTEM

BACKGROUND OF THE INVENTION

1. Field of the Invention

The present invention relates to methods and systems for the computer aided diagnosis (CAD) of abnormalities and digital processing of radiological images. More specifically, the present invention relates to a user interface for an automated method and system for the re-screening and detection of abnormalities.

2. Background Art

Computer-aided diagnosis (CAD) systems use digital processing methods to assist users in the identification of abnormalities. U.S. Pat. No. 5,917,929 describes a user interface for facilitating the input of films into a CAD system. The user interface includes a scanner that receives and scans the film-based images and a film feeder that holds and transports them to the scanner. A touch-sensitive display screen is provided to display status information to and receive instructions from an operator. The display screen displays miniature images of the films having color-coded borders, the colors indicating to the operator the stage of the processing of the films. The interface also includes a bar code reader and allows the operator to conduct procedures for testing the scanner. However, there are a number of capabilities, in addition to the above, that could be furnished, but are not.

SUMMARY OF THE INVENTION

The object of the current invention is to provide a more flexible user interface for a CAD system with greater capabilities than in prior art user interfaces. More specifically, the current invention has as its objects at least the following: (1) to allow the user to change diagnosis results from the output of the CAD system; (2) to allow the user to manipulate images after the CAD processing; (3) to allow the CAD processor to connect to an image acquisition device such as a film developer, film digitizer or phosphor-plate scanner directly without human interface; (4) to allow the CAD processor to connect to multiple image acquisition devices; and (5) to allow the entry of multiple image identification for multiple image scanning.

In one embodiment, the present invention comprises a user interface including an input interface. The input interface may accommodate both image inputs and data inputs. To accommodate image input, the input interface may comprise at least one film feeder and at least one image acquisition device. It may further comprise multiple image feeders and scanners. At least one of the image feeders and/or scanners may receive input directly from an image developer. The input interface may further comprise means by which to receive digital image inputs, including via wireless communications and via computer networks.

To accommodate data inputs, the input interface may comprise a keyboard, a keypad, a mouse, a bar code reader, and/or other input devices. It may further include a voice interface and/or a writing interface (e.g., a digital tablet). Such data inputs may also be furnished via wireless means or via computer networks.

In another embodiment, the invention comprises an output interface including display means. The display means may include small "thumbnail" displays of multiple images, and it may also include a large display of a single image. The display may include indications of suspected abnormalities detected by CAD processing. The display may further accommodate user-identified user-accepted, and user-deleted abnormalities, entered using an input interface.

The output interface may further include displays of image data and of comments entered by a user. It may also include options and displays for use in conjunction with an input interface.

Definitions

In describing the invention, the following definitions are applicable throughout (including above).

A "computer" refers to any apparatus that is capable of accepting a structured input, processing the structured input according to prescribed rules, and producing results of the processing as output. Examples of a computer include a computer; a general-purpose computer; a supercomputer; a mainframe; a super mini-computer; a mini-computer; a workstation; a microcomputer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

A "computer-readable medium" refers to any storage device used for storing data accessible by a computer. Examples of a computer-readable medium include a magnetic hard disk; a floppy disk; an optical disk, like a CD-ROM or a DVD; a magnetic tape; a memory chip; and a carrier wave used to carry computer-readable electronic data, such as those used in transmitting and receiving e-mail or in accessing a network.

"Software" refers to prescribed rules to operate a computer. Examples of software include software; code segments; instructions; computer programs; and programmed logic.

A "computer system" refers to a system having a computer, where the computer comprises a computer-readable medium embodying software to operate the computer.

A "network" refers to a number of computers and associated devices that are connected by communication facilities. A network involves permanent connections such as cables or temporary connections such as those made through telephone or other communication links, or both. Examples of a network include an internet, such as the Internet; an intranet; a local area network (LAN); a wide area network (WAN); and a combination of networks, such as an internet and an intranet.

A "computer-aided diagnosis (CAD) system" is a computer system that:

receives patients' diagnosis images such as patients' x-ray images, pap smears, mammograms, or the like;

processes patients' diagnosis images; and generates CAD results indicating either potential abnormalities at specific locations (for example, the location of a disease) in the patients' diagnosis images or potential abnormalities appearing on entire patients' diagnosis images. (CAD usually only indicates that the image may have some abnormality but does not specify the specific location on the image.)

A physician or other health care provider can use the CAD results along with other tools and information to determine the specifics and locations of diseases for the patients.

BRIEF DESCRIPTION OF THE DRAWINGS

Embodiments of the invention will now be described in conjunction with the accompanying drawings, in which.

DESCRIPTION OF EMBODIMENTS OF THE INVENTION

In this disclosure, a chest X-ray based CAD system is used as an example. The invention is not, however, limited to such a system, but is applicable to CAD systems, in general. Furthermore, the embodiments described here involve a single processing unit connecting with one or multiple image acquisition devices; however, the invention is also applicable to a configuration consisting of multiple processing units.

The invention comprises a method and system for providing interfaces with a CAD system. Such interfaces include both input and output interfaces.

Figure 1:
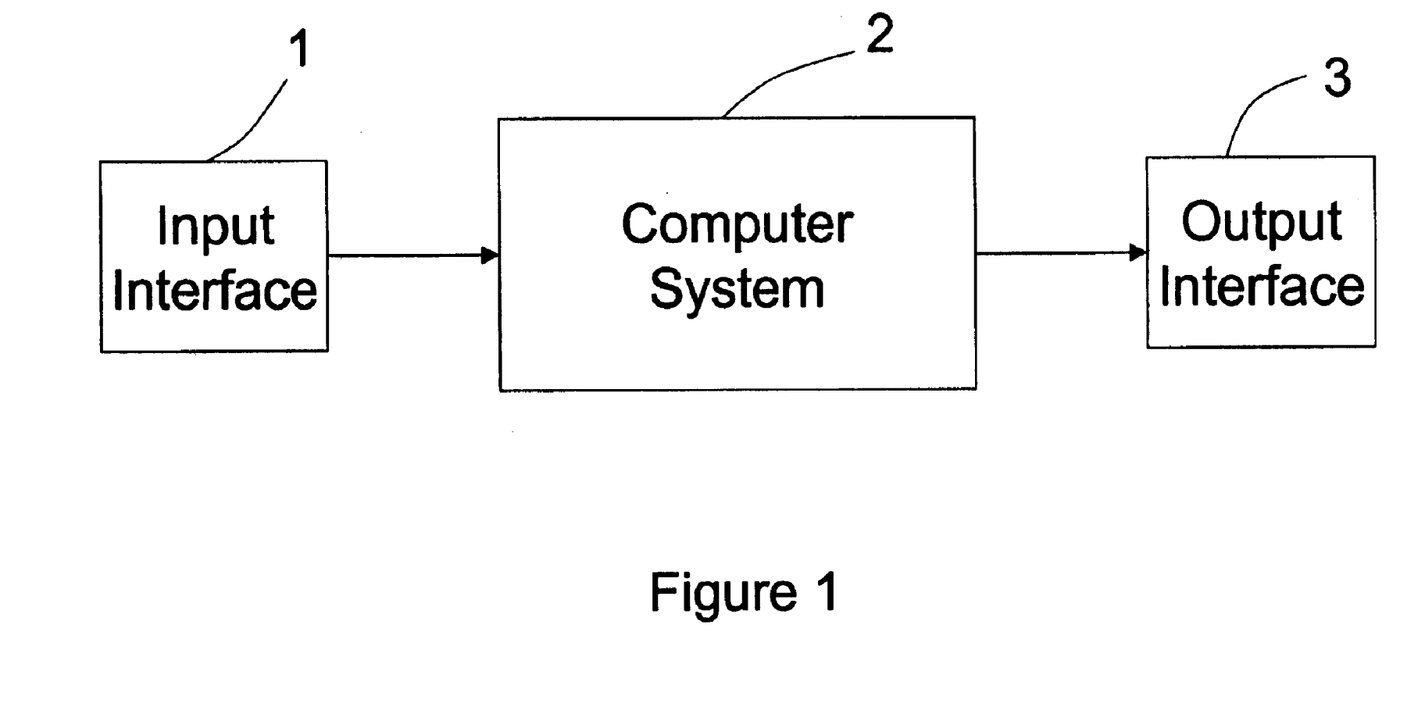
FIG. 1 shows a general block diagram of a CAD system.

FIG. 1 shows a block diagram of a typical CAD system. The heart of the system is a computer system 2, which runs software implementing the CAD functionality. Data from users and/or other systems enters computer system 2 through input interface 1. Computer system 2 provides outputs through an output interface 3. While input interface 1 and output interface 3 are shown as separate blocks, they may be combined as a single input/output interface.

Input interface 1 may comprise a number of different input devices. Computer system 2 may have the capability of interacting with only a single input device; however, it will typically be capable of interacting with multiple input devices. In general, there are two types of inputs: user input (e.g., alphanumeric data, bar code data, selections/instructions, marks of user-identified or other-devices-identified abnormalities, and the like) and image data (e.g., X-ray images, computer tomography (CT) images, and the like). Input interface 1 will generally include means for facilitating both types of inputs.

Figure 2:
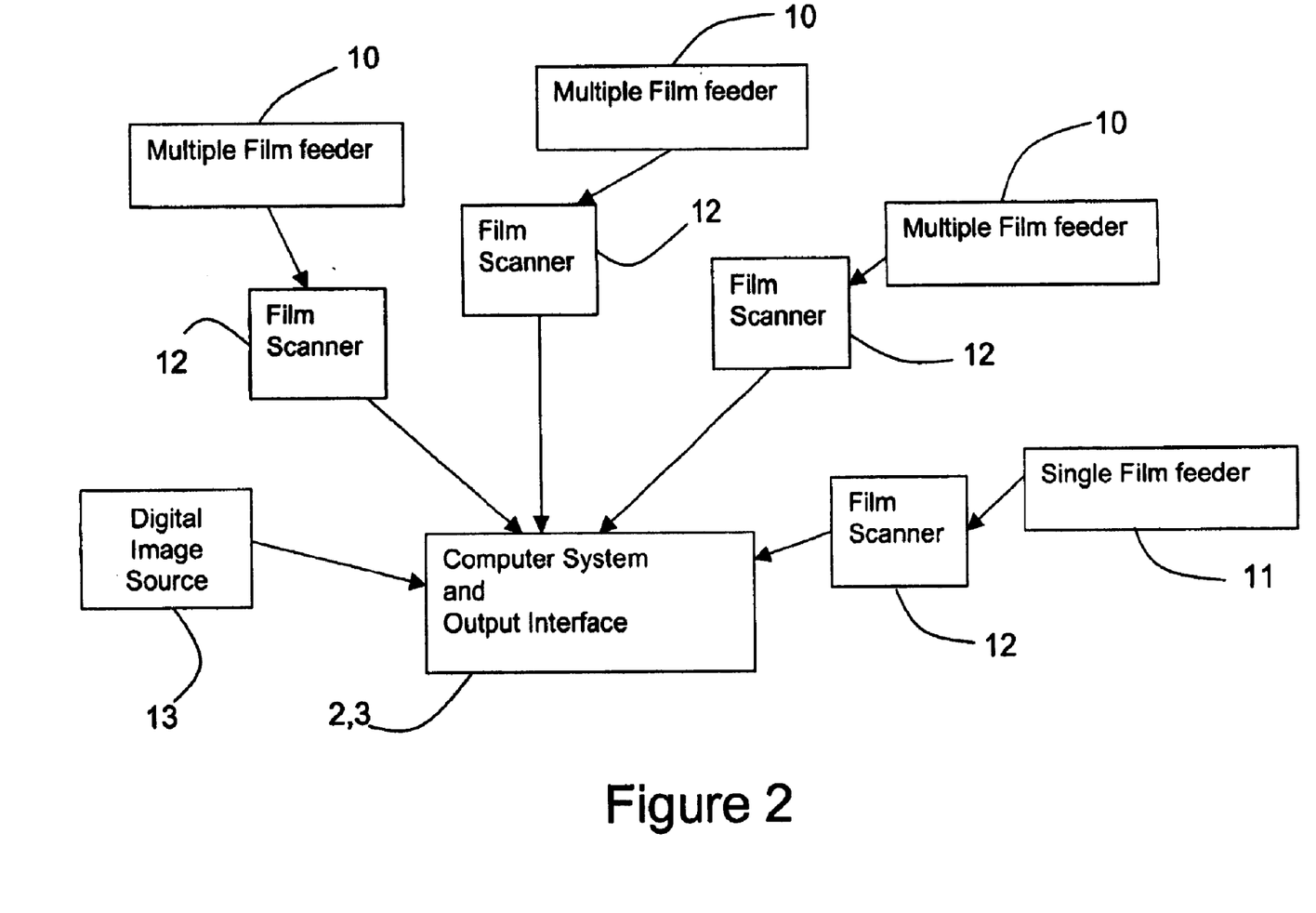
FIG. 2 shows a block diagram of a CAD system according to one embodiment of the invention, showing an exemplary embodiment of an input interface.

FIG. 2 shows a block diagram of a computer system capable of receiving input from multiple image input devices. In FIG. 2, computer system 2 and output interface 3 are shown as a single block, labeled "2, 3", for convenience. As shown in FIG. 2, image input devices are connected to the system 2, 3 and provide source interfaces with multiple image sources. These devices may include single film scanners 11, 12 or multiple film scanners 10, 12 or other image acquisition devices, which would include digitization if the images were not already in digital form. For example, digital image data may be input directly from a digital image source 13. Such other image acquisition devices are intended to include, for example, means for receiving wireless transmissions of images and means for receiving images from a computer network. As shown, a multiple film scanner can be a single scanner 12 with multi-film feeder 10, or several scanners 12, each with a single film feeder 11, or multiple scanners 12, each with a multi-film feeder 10.

There are several types of film scanners on the market. One exemplary type is a laser scanner made by Lumysis (now part of Kodak). The Lumysis scanner emits laser light and uses a photo multiplier to acquire the signal. Another type of scanner is a CCD scanner, like those produced by Howtek and Vidar. The Vidar scanner emits fluorescence light and uses a CCD to acquire the image, whereas the Howtek scanner emits narrow-bandwidth light and uses a CCD to acquire the image. The Vidar scanner, used in an exemplary system embodiment, can accept up to twenty-five films at a time in its feeder.

Figure 3:
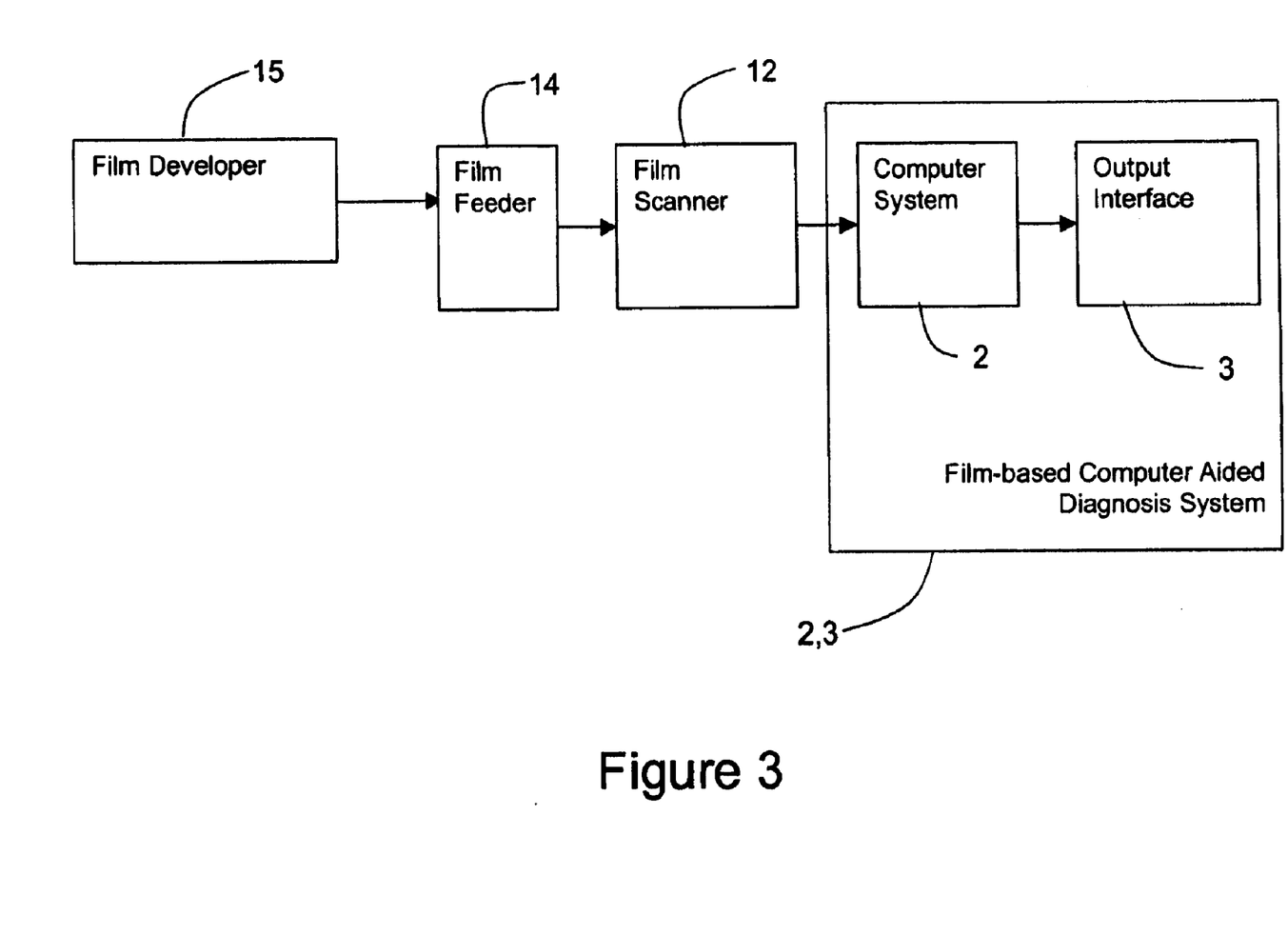
FIG. 3 shows a block diagram of a CAD system according to an embodiment of the invention.

Yet another image input possibility for a film-based CAD system is for a film scanner to be directly connected to a film processor. This is shown in FIG. 3. As shown, film developer 15 is connected to film feeder 14, which may be either a single film feeder or a multiple film feeder. As in FIG. 2, film feeder 14 feeds the film(s) to a film scanner 12, which provides image input to the CAD system 2, 3. Thus, developed films are thereby automatically sent to the CAD system and processed.

Figure 4:
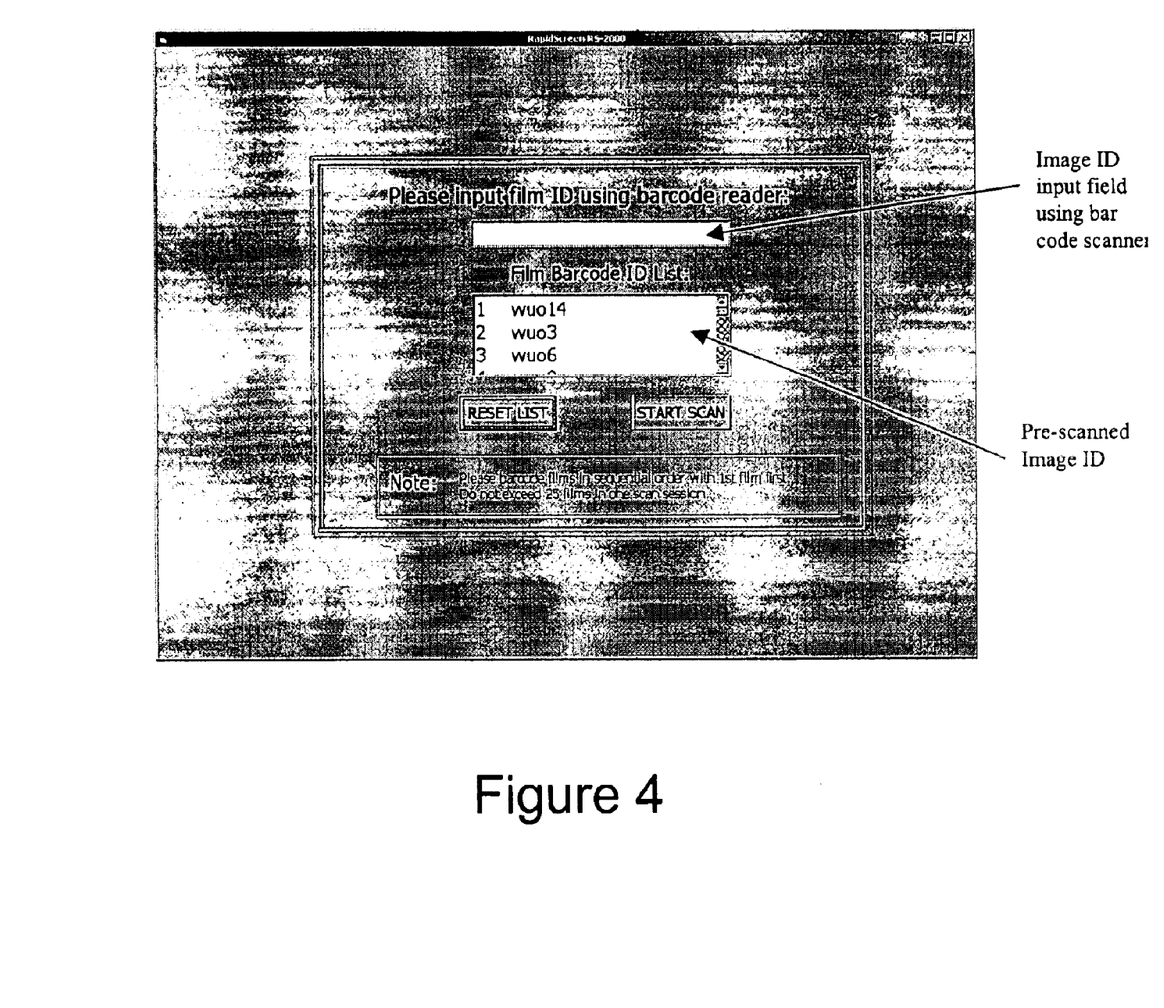
FIG. 4 shows a screen shot demonstrating an embodiment of an interface for inputting image ID numbers using bar codes.

Input interface 1 may further facilitate multiple image ID management using bar codes or data entered using a numeric keypad, keyboard, network (for example, over an Internet connection), or other input devices. FIG. 4 shows an exemplary implementation of the invention using a bar code image ID input function (i.e., FIG. 4 is a screen shot of what would be displayed to the user; the display itself is technically part of output interface 3). In this implementation, a user can use bar codes to input multiple image IDs prior to the film scanning (or other image input). The user may, alternatively, use a keyboard, keypad, or other means for inputting image IDs. During film scanning (image input) processing, each ID will be assigned to each digitized image in a pre-sorted order or according to some other predetermined order, which may be determined by a user.

As discussed above, input interface 1 also generally includes devices to facilitate user input. Such devices may include, for example, a numeric keypad, a keyboard, a mouse, an electronic pen, a touch screen (which would be a hybrid input interface 1/output interface 3), or a voice interface. Inputs made using such devices may be used for either or both purposes of inputting data about images and inputting information necessary to run the CAD system (e.g., telling the system to run, entering parameters, accepting and rejecting marks/indications associated with abnormalities identified by the CAD system, adding a new mark/indication identified by the user, selecting images, etc.). In the case of a voice interface, exemplary voice interfaces include a voice-activated device that could be used to operate the CAD system and/or a voice recording device to record a physician's diagnosis or other comments.

Output interface 3 generally consists of all devices providing output to the system user. Such devices may include monitors, touch screens, audio speakers, or any other output devices. Output interface 3, together with input interface 1 permits a user to initiate, control, and review and manipulate results of CAD processing.

A particular embodiment of an output interface 3 of a CAD system according to the present invention allows a user, in either a new diagnosis result or result modified from the CAD result, to Accept CAD results by keeping some or all CAD results;
Reject CAD results by removing some or all CAD results;
Add new diagnosis result(s);
Apply any combination of the above to generate a final diagnosis result.

Particular embodiments of output interface 3 that support these functions will be discussed below.

Figure 5:
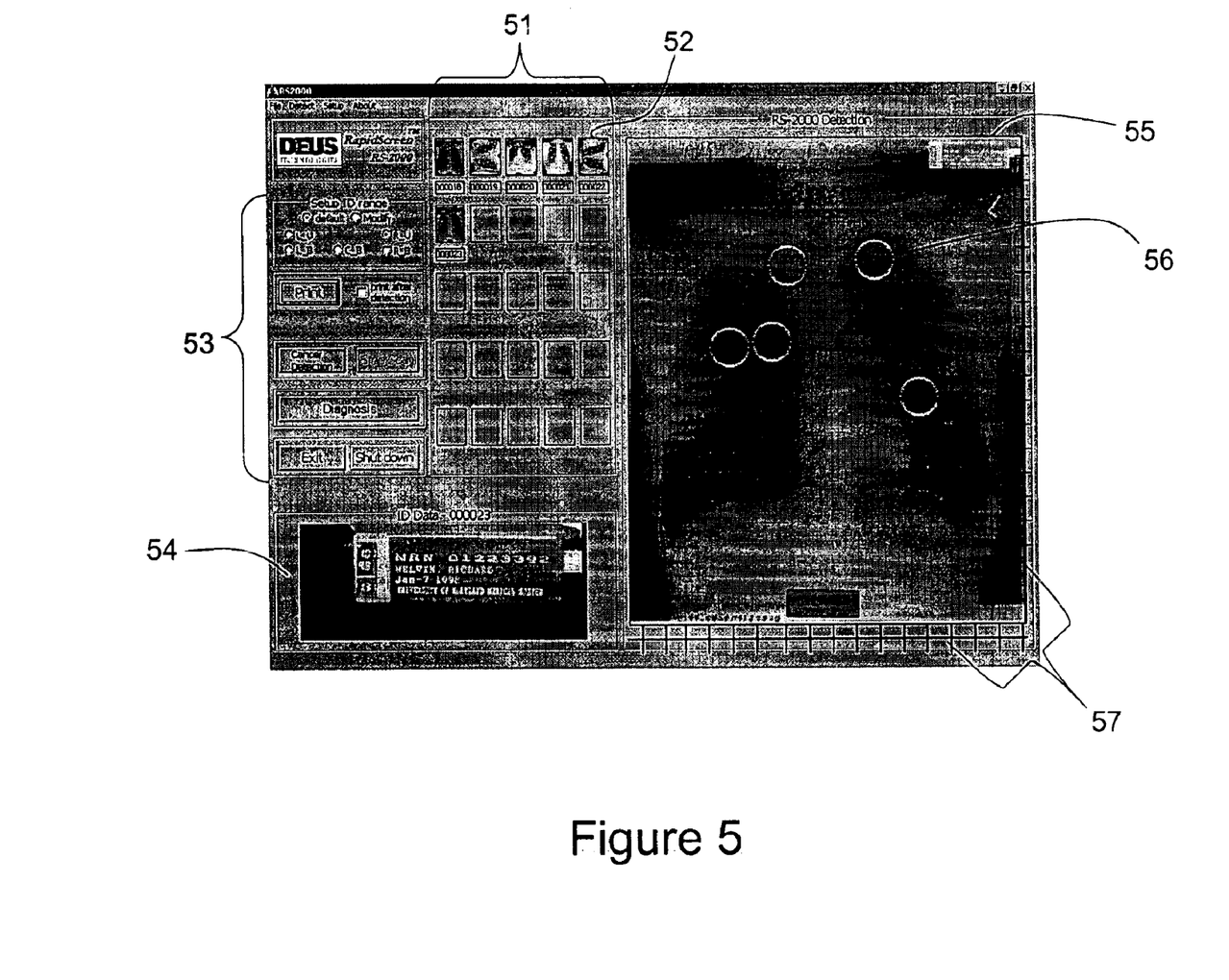
FIGS. 5–8 show screen shots demonstrating embodiments of an output interface according to the invention.

FIG. 5 shows a screen shot depicting exemplary features for implementing the functions discussed above. FIG. 5 includes a mosaic arrangement/image management display 51 consisting of multiple thumbnail images, where a display of image identification data is included for each image. The individual thumbnail images may be implemented with means by which to indicate processing status to a user; this may be done in a number of ways. For example, in U.S. Pat. No. 5,917,929, a border 52 of each thumbnail image takes on a different color at each stage of processing. This could be similarly implemented using a dot that turns a different color to indicate each stage of processing. Alternatively, a number of different colored dots could be used for each image, with each color associated with a different stage of processing; in this implementation one dot, indicating the current stage of processing for the image, would be brighter than the others (similar to colored lights being turned on and off). In another embodiment, this function is implemented by means of an alphanumeric display associated with each thumbnail image, the alphanumeric display indicating the stage of processing of the associated image; this may be in the form of a statement of the stage of processing or a code indicating the stage. In yet another embodiment, the display indicating the stage of processing may be in the form of a pictorial display for each thumbnail image including one or more symbols indicating the stage of processing.

The thumbnail images in FIG. 5 may be replaced by a text-only displays for the images, in an alternative embodiment of the invention.

FIG. 5 also includes an image display 55 of a CAD result or other image. Image display 55 preferably comprises at least one-fourth of the total available area of the screen, in order to provide the user with an image suitable for careful inspection. The image to be displayed in the image display 55 may be selected by a user. Image display 55 may also be outfitted with scale indicators 57. Scale indicators 57 may be provided in units of inches, centimeters, etc.; in an exemplary embodiment of the invention, the units are user-selected. In an exemplary embodiment of the invention, image display 55 may be capable of supporting various output image resolutions (for example, 37.5, 75, 150, 300, 600 dpi); furthermore, the output image resolution may be user-selectable.

When the image displayed in the image display 55 represents a CAD output, the results of CAD processing will generally be displayed on the image. In FIG. 5, suspected abnormalities, as determined by a CAD system, are shown surrounded by circles 56. Other shapes may alternatively be used.

The screen shown in FIG. 5 also includes an information display field 54. Information display field 54 may be used to display, for example, date, time, operator, patient ID number, or other similar information. In FIG. 5, information display field 54 shows an exemplary embodiment in which the information displayed is taken from a portion of an image input indicating such information as previously described.

The output interface 3 may also serve as part of input interface 1. In FIG. 5, a display of options 53 contains several different "buttons" for selection by a user, using an input device (e.g., mouse, electronic pen, etc.). In the exemplary embodiment shown, the user can perform such functions as setting up an ID range, requesting a printout, directing the system to perform cancer detection, etc.

Output interface 3 may enable the user to perform numerous types of post-processing manipulation of CAD results.

Figure 6:
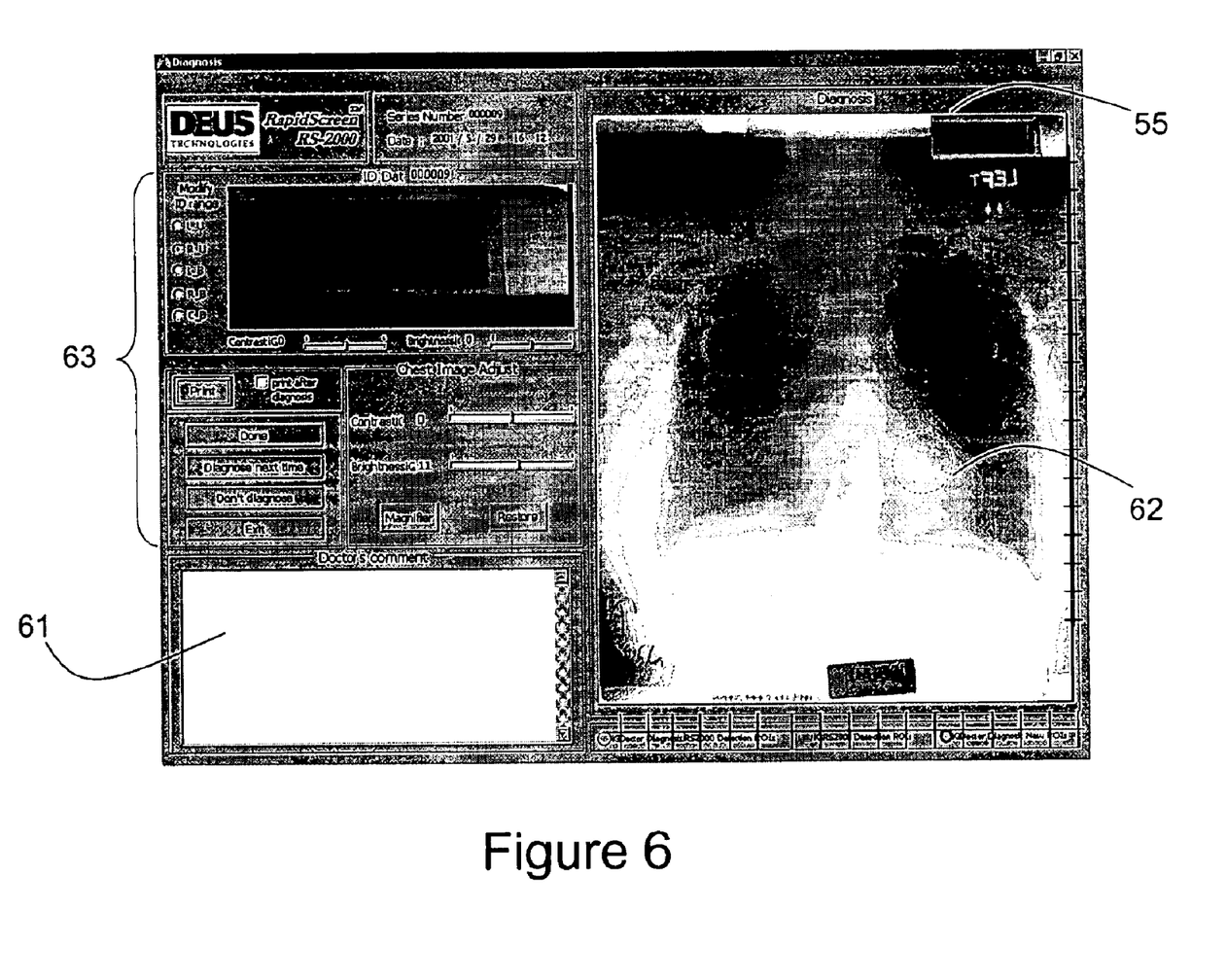

FIG. 6 depicts a screen shot showing display of an image after CAD processing is complete. Image display 55 again contains an image, and the image is now a diagnosis image that includes indications of potential abnormalities (e.g., as indicated by reference numeral 62) identified by the CAD processing. Potential abnormalities may be indicated not only by encirclement, as shown, but by any other means; for example, any shape (not just circles) may be used, arrows may be used, coloring may be used, etc.

The output interface shown in FIG. 6 also provides a display 61 for showing comments provided by a user (e.g., a physician). The user may enter such comments by any known means, for example, a keyboard, a keypad, a voice interface, a handwriting interface (tablet), a bar code reader, etc. Such comments 71 are shown, for example, in FIGS. 7 and 8.

Figure 7:
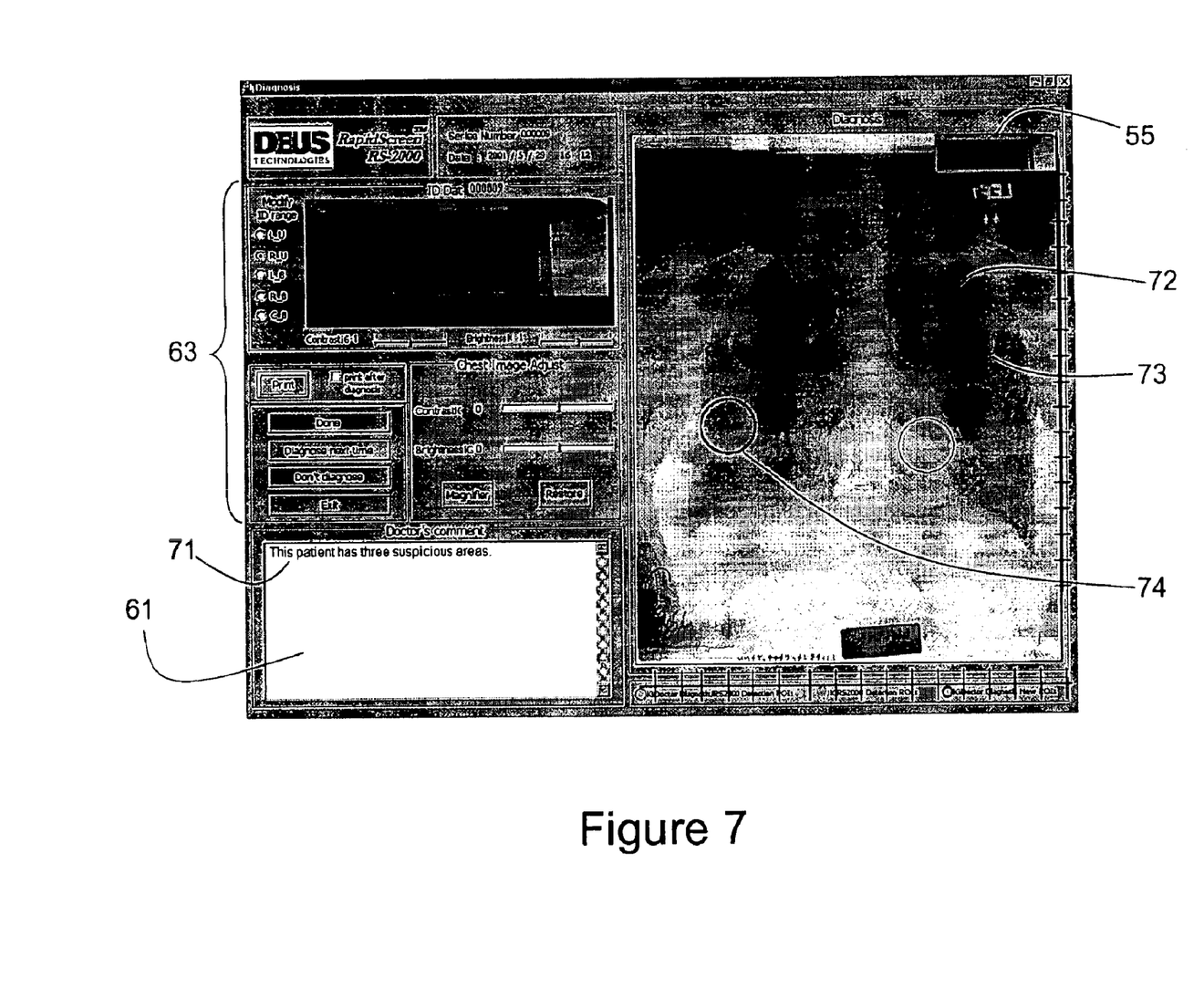
Figure 8:
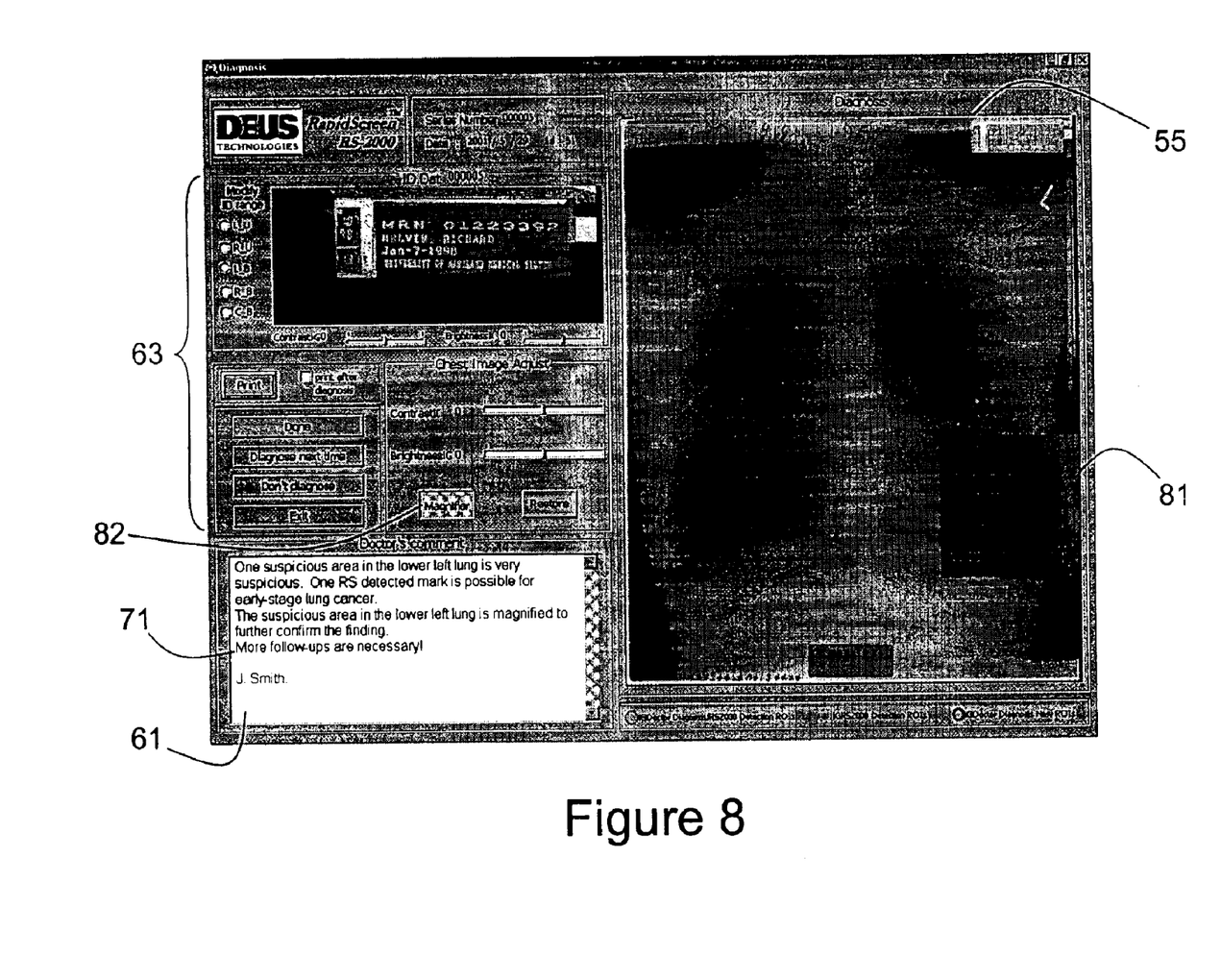

The output interface 3 as shown in FIGS. 6–8 also includes a field 63 having an image data display and a display of options that includes various input options. These input options permit, for example, printouts, image manipulation, and other post-processing functionalities. Image manipulation techniques implemented may include, for example, zoom in/out (i.e., magnification), masking, image rotation, etc. FIG. 8, in particular, shows a case in which a user has selected magnification button 82 in order to look at a particular region 81 of image display 55 in greater detail.

Another important function enabled by output interface 3 is what may be termed, "result editing." Such result editing involves the user reviewing the CAD findings (as shown, e.g., by reference numeral 62 in FIG. 6) and making decisions regarding them. The user may agree or disagree with the CAD findings, may delete any or all of them, and may add his or her own diagnostic findings to the image, using a pointing device (e.g., mouse, electronic pen, etc.). FIG. 7 depicts one exemplary way in which such result editing might be implemented. In image display 55, a CAD result that is confirmed (i.e., agreed with) by a user is shown having thin encirclement 72. A CAD result that is discarded (i.e., disagreed with) by a user is shown having dashed encirclement 73. Finally, a user diagnosis, not detected by CAD processing, is shown having thick encirclement 74. Many other methods of such indications (e.g., different shapes, different colors, etc.) are possible. The results of the result editing can then be stored as the final results, along with any comments 71 the user may have.

The output interface shown in FIGS. 6–8 may enable additional functions. For example, a user may select a small region of interest and have the CAD system compute feature parameters on that small region. The user may also select a region of interest and have the CAD system re-examine that region. As with the initial output images from the CAD system, the resulting output images from such operations are then linked to output interface 3 for further examination by the user.

The invention has been described in detail with respect to preferred embodiments, and it will now be apparent from the foregoing to those skilled in the art that changes and modifications may be made without departing from the invention in its broader aspects. The invention, therefore, as defined in the appended claims, is intended to cover all such changes and modifications as fall within the true spirit of the invention.

What is claimed is:

1. An input/output interface for a computer-aided diagnosis (CAD) system, the input/output interface comprising:
   an input interface; and an output interface comprising:
   a display simultaneously comprising the following:
      an image display;
      an image data display;
      a display of options selectable via the input interface; and
      an image management display containing information pertaining to at least an image shown in said image display, wherein the image management display comprises a display capable of displaying at least two miniature images, including an image being displayed in the image display, and wherein the display capable of displaying at least two miniature images further includes means for indicating a status of processing of each respective miniature image, said processing comprising at least two stages.

2. The input/output interface of claim 1, wherein the display capable of displaying at least two miniature images further includes a display of image identification data for each miniature image.

3. The input/output interface of claim 1, wherein the image display includes scale indicators.

4. The input/output interface of claim 3, wherein the scale shown on the scale indicators is user selectable.

5. The input/output interface of claim 1, wherein the image display comprises a display supporting multiple image resolutions.

6. The input/output interface of claim 5, wherein the input/output interface includes means permitting a user to select an image resolution of the display supporting multiple resolutions.

7. The input/output interface of claim 1, wherein the image management display comprises a display of comments entered by a user via the input interface.

8. The input/output interface of claim 1, wherein the display of options selectable via the input interface includes at least two of the following options: setup ID range, print, cancer detection, diagnosis, exit, and shut down.

9. The input/output interface of claim 1, wherein the display of options selectable via the input interface includes at least two of the following options: print, done, diagnose next time, don't diagnose, exit, and image adjust.

10. The input/output interface of claim 9, wherein image adjust comprises at least one of the following: contrast adjustment, brightness adjustment, and magnification.

11. The input/output interface of claim 1, wherein the image data display includes options selectable via the input interface, including at least two of the following: modify ID range, contrast adjustment, and brightness adjustment.

12. A CAD system comprising the input/output interface of claim 1 and a computer system running software for performing CAD processing.

13. The input/output interface of claim 1, wherein the means for indicating a status of processing of each respective miniature image comprises a display associated with the miniature image, the display comprising at least one visual indication of a present stage of said processing.

14. The input/output interface of claim 13, wherein the at least one visual indication comprises a color corresponding to said present stage of said processing.

15. The input/output interface of claim 13, wherein the display comprises an alphanumeric display associated with the miniature image, the alphanumeric display indicating a stage of processing of the miniature image as at least one said visual indication.

16. The input/output interface of claim 13, wherein at least one visual indication comprises at least one symbol corresponding to said present stage of said processing.

17. An input/output interface for a computer-aided diagnosis (CAD) system, the input/output interface comprising:
   an input interface; and
   an output interface comprising:
      a display simultaneously comprising the following:
         an image display;
         an image data display;
         a display of options selectable via the input interface; and
an image management display containing information pertaining to at least an image shown in said image display, wherein the image management display comprises a display capable of displaying at least two miniature images, including an image being displayed in the image display, and wherein the display capable of displaying at least two miniature images further includes at least one indicator of a status of processing of each respective miniature image, said processing comprising at least two stages.

18. The input/output interface of claim 17, wherein the at least one indicator of a status of processing of each respective miniature image comprises a display associated with the miniature image, the display comprising at least one visual indication of a present stage of said processing.

19. The input/output interface of claim 18, wherein the at least one visual indication comprises a color corresponding to said present stage of said processing.

20. The input/output interface of claim 18, wherein the display comprises an alphanumeric display associated with the miniature image, the alphanumeric display indicating a stage of processing of the miniature image as at least one said visual indication.

21. The input/output interface of claim 18, wherein the at least one visual indication comprises at least one symbol corresponding to said present stage of said processing.

* * * * *